United States Patent [19]

Peleg

[11] Patent Number: 5,691,473

[45] Date of Patent: Nov. 25, 1997

[54] METHOD AND EQUIPMENT FOR MEASURING FIRMNESS OF FRUITS AND VEGETABLES

[76] Inventor: Kalman Peleg, 311 Spinnaker Str., Foster City, Calif. 94404

[21] Appl. No.: 898,446

[22] Filed: Jun. 15, 1992

Related U.S. Application Data

[63] Continuation-in-part of Ser. No. 503,689, Apr. 3, 1991, abandoned.

[51] Int. Cl.[6] ............................................. G01N 33/02
[52] U.S. Cl. ........................... 73/573; 73/579; 209/599
[58] Field of Search .............................. 73/573, 579, 580, 73/599; 209/590, 599

[56] References Cited

U.S. PATENT DOCUMENTS 4,884,696  12/1989  Peleg ..................................... 209/599

FOREIGN PATENT DOCUMENTS

| | | | |
|---|---|---|---|
| 1-217255 | 8/1989 | Japan | 209/599 |
| 1-274059 | 11/1989 | Japan | 73/579 |
| 513266 | 5/1976 | U.S.S.R. | 73/579 |
| 550556 | 4/1977 | U.S.S.R. | 73/573 |

*Primary Examiner*—John E. Chapman

[57] ABSTRACT

The invention relates to non-destructive measurement of the firmness of fruits and vegetables, particularly to methods and equipment for measuring the firmness of such edible objects in order to establish their ripeness or maturity stage, not only after they have been harvested or stored, but also during the growing process. The method comprises:- 1) gripping the object in two substantially diametrical points between two gripper bodies at a predetermined pressure, 2) applying a vibrational excitation onto one of the two points by means of a vibration actuator using a composite signal with predetermined frequency content, amplitude range and phase shift configuration, specialized for the kind of fruit to be tested, 3) measuring the input signal by means of a first acceleration transducer attached to a gripper body on the vibration actuator contacting one side of said object 4) measuring the output signal on the other side of said object by means of a second acceleration transducer attached to an opposite gripper body, 5) passing the signals through a difference amplifier and obtaining a relative acceleration signal by deducting the input signal from the output signal, 6) feeding the obtained signals to computer means and obtaining a firmness index by the quotient of the root mean square of the output acceleration signal divided by the root mean square of the relative acceleration signal. The equipment may comprise manually or automatically operated table-top or hand-held "FIRMNESS TESTERS" or "FIRMNESS SENSORS" that can be mounted as robotics end-effectors or incorporated in a cup-conveyor line for automatically sorting fruits and vegetables by firmness, in a packinghouse.

24 Claims, 11 Drawing Sheets

METHOD AND EQUIPMENT FOR MEASURING FIRMNESS OF FRUITS AND VEGETABLES

This is a continuation-in-part of specification Ser. No. 503,689, filed Apr. 3, 1991 now abandoned.

BACKGROUND OF THE INVENTION

The invention relates to the non-destructive measurement of the firmness of various fruits and vegetables. It relates more particularly to methods and equipment for measuring the firmness of such edibles in order to establish their ripeness or maturity stage, not only after they have been harvested or stored, but also during the growing process on the tree, wine or in the field, in order to determine the optimal harvest time or effect selective picking of ripe fruits while leaving the non-ripe fruit for a later harvest.

The ripeness and maturity of many fruits and vegetables is directly related to their firmness. Relatively soft fruit, such as peaches, apricots, tomatoes, can be classified according to firmness by a human sorter, on a relative basis by pressing or squeezing them by hand. This is an expansive labor intensive task frequently involving some damage to the fruit. In relatively firm fruit, such as apples, avocado, potatoes, melons, watermelons, cantaloupes, a human sorter cannot distinguish between freshly picked "firm-ripe" fruit and "soft over-ripe" fruit, since even the latter is still too hard for easy deformation by hand. In these fruit types it is common practice to pierce fruit samples by a penetrometer tool employing a conical or plunger-shaped head, whence the mean piercing force of the sample, is indicative of its firmness. This method can, evidently, not be used for testing all fruits, especially for selective harvesting and monitoring the ripeness stage of the produce in storage, or on a packinghouse production line, where a non-destructive method of measuring firmness is imperative.

In my U.S. Pat. No. 4,884,696 I described a cup conveyor provided with various sensing apparatus for automatically inspecting and classifying a stream of different objects, particularly fruits and vegetables, including devices for transferring the classified objects onto separate conveyors.

This apparatus includes sensors for measuring various mechanical properties as well as resistance to applied force, contact pressure, frequency response and energy dissipation. For the purpose of measuring the firmness of spherical or otherwise shaped objects, the cups in the above conveyor system are provided with an opening in their bottom portion, permitting contact of a vibration actuator with the bottom of the object, while the top of the object is brought into contact with a response acceleration transducer attached to the end of a leaf-spring serving as a gripper element.

Firmness of the object is indicated by measuring the output acceleration and comparing it with the input acceleration by suitability programmed computer means. The conveying system may also include gripper pads provided with a force-load cell for measuring and controlling the force exerted on the objects by said gripper and for classifying, such as fruit, in accordance with their firmness and force-deformation characteristics. These devices are suitable for sorting and grading fruits in a packinghouse processing line and are highly sophisticated, since every object passes the respective sensing apparatus within a very short time interval; they are, therefore, not suitable for inspecting stored samples of individual fruits and vegetables or during their growing process in the field or on the tree, where a handy and light tool is imperative.

The fruit gripping device in said U.S. Pat. No. 4,884,696 is suitable for handling different produce types, provided that the size range of the tested fruits is rather narrow. For switching between different fruit types and size ranges it is required to replace the entire gripping device, each adapted for a particular size range of fruits or vegetables.

It is, for these reasons, the object of the present invention to provide fruit and vegetable firmness testing equipment which is portable and may be optionally connected to a domestic electric supply system or be independent of it by the use of electric rechargeable batteries.

It is another object to provide said equipment in bench-top configurations for measuring firmness of samples of individual fruits and vegetables, as well as in hand-held or robotics end effector configurations for measuring firmness of ground-growing produce, such as melons and cantaloupes or tree growing fruits, such as apples and avocado.

It is still another object to provide the equipment with simple electronic circuitry and computing means, using readily and cheaply obtainable chips and components, capable of computing and displaying digital readout of firmness values and simple statistics, as well as portable data logging means for further processing by a computer.

It is further another object to provide the equipment with a capability for enabling manual or mechanized selective harvesting, by issuing command signals in respect of the firmness or ripeness of the examined produce, for activating simple marking means in order to automatically identify soft an firm fruits or issue appropriate electrical, audible or visual signals.

There is still another object to implement improved gripper body shapes and gripper arm configurations as well as permit manual or automatic adjustment of the gripper to any fruit size, not only in said portable equipment, but also in the automatic packinghouse machine described in my U.S. Pat. No. 4,884,696.

There is further another object to implement manual adjustment or automatic control of the gripping force acting on the fruit and vegetable during the firmness testing interval.

And there is still another object to implement an improved firmness index and vibration excitation signals, which will enable measuring firmness with better accuracy, not only by said portable equipment, but also by the automatic packinghouse machine described in my U.S. Pat. No. 4,884,696.

And it is a final object to provide simplified versions of said portable firmness testing equipment at low cost so as to permit fruit and vegetable growers, shippers, processors and fruit and vegetable stores to purchase it for their daily use.

SUMMARY OF THE INVENTION

The method of testing the firmness of one single fruit or vegetable, either freshly picked, after storage or still on the tree or in the field comprises:

1) gripping the fruit or vegetable in two substantially diametrical points between two gripper bodies at a predetermined pressure or force on the fruit or vegetable,
2) applying a vibrational excitation onto one of the two points by means of a vibration actuator using a composite signal with predetermined frequency content, amplitude range and phase shift configuration, specialized for the kind of fruit or vegetable to be tested,
3) measuring the input signal by means of a first acceleration transducer attached to a gripper body on the vibration actuator contacting one side of the fruit or vegetable, 4) measuring the output signal on the other side of the fruit or vegetable by means of a second acceleration transducer attached to an opposite gripper body, 5) passing the signals through a difference amplifier and obtaining a relative acceleration signal by deducting the input signal from the output signal, 6) feeding the obtained signals to analog and/or digital computer means and obtaining a firmness index by the quotient of the root mean square of the output acceleration signal divided by the root mean square of the relative acceleration signal.

A preferred embodiment of a "table-top" firmness tester essentially includes a flat base or a self contained frame and a vibration actuator bolted thereto, provided with a first vibrating gripper body and a second movable gripper body for engagement of the object, such as a fruit or vegetable, in approximately diametrically positioned opposite points. The vibration actuator is adapted to excite the object on one side by a composite excitation signal characteristic in frequency content, amplitude values and phase shift configuration, optimized for each fruit and vegetable type. The second gripper body is mounted on one end of a leaf-spring, the other end of which is connected to a gripper arm which may be moved manually or automatically to engage the other side of the object thereby gripping the object between said vibrating and movable gripper bodies. The movement of the gripper arm may be effected by a rotary trajectory or a linear trajectory as well as a combination of linear and rotary motion. The means for moving said gripper arm may be adapted to be operated manually, or automatically by an electric motor, pneumatic actuator or hydraulic actuator. Strain gauges incorporated in the leaf spring or a load cell attached between the gripper arm and the leaf spring emit a signal proportional to the gripping force. When the gripper arm is moved manually, a predetermined object gripping force is effected by observing the magnitude of this signal on a voltmeter readout. When the gripper arm is moved automatically, as by an electric stepping motor, this signal is used in a control loop configuration for automatically maintaining a preset gripping force. In any case the magnitude of the gripping force is just sufficient to transmit the vibration signal through the fruit or vegetable without causing any damage thereto.

An acceleration transducer is attached to the first gripper body and is adapted to measure the input acceleration and to issue a first signal characteristic of the input acceleration;

a second acceleration transducer is attached to the second gripper body and is adapted to measure the output acceleration transmitted through the object and to issue a second signal characteristic of the output acceleration. The two signals are fed to a difference amplifier, producing a signal denoting the relative acceleration in real time. The fruit firmness index is then computed by analog or digital computer means as a ratio of the root mean square values of the output acceleration and the relative acceleration. Electric power is supplied to the firmness tester and the computer means either from a domestic supply or rechargeable batteries.

A preferred embodiment of an "automatic rotary gripper arm table-top firmness tester" adapted for automatically moving the gripper arm in a rotary trajectory includes a flat base to which the vibration actuator is bolted at one end and a pedestal post holding a rotary electric stepping motor, height adjustable for different size ranges of fruits and vegetables. The base also includes electric connectors to external signal conditioning electronics and computer means, or a circuit board incorporating customized signal conditioning circuity and computer means is mounted on the base proper.

A preferred embodiment of a "manually operated rotary gripper arm table-top firmness tester" adapted for manually moving the gripper arm in a rotary trajectory includes said flat base and vibration actuator but in lieu of said stepper motor the pedestal post is adapted to carry a height adjustable bearing housing and shaft, with a manually operated wheel.

A preferred embodiment of a "linear gripper arm motion table-top firmness tester" adapted for moving the gripper arm in a linear vertical trajectory comprises a self contained frame configuration. The lower elongated horizontal part of said frame serves the same purposes as the above flat base, while the vertical part incorporates a platen and a slider body, which is guided along the platen on rows of steel balls or miniature ball bearing rollers traveling on the sides of the platen. A strong permanent magnet incorporated in the slider body causes it to be attracted to the platen at all times, essentially serving as a magnetic brake, so that the slider position along the platen is fixed unless it is displaced from this position by an external force which is stronger than the magnetic field forces. The gripper arm is attached to the slider body wherein for gripping a fruit or vegetable the slider body may be moved up or down the platen manually, or automatically. Manual operation is effected by a hand operated lever attached to the slider body. Automatic movement of the slider body is effected by a pair of windings, one of which is located in the slider body, on one side of said permanent magnet, while the other is located on the other side of said permanent magnet, substantially as in a "forcer" of a conventional linear electric stepping motor. To allow micro-stepping motion of the slider body, said platen surface incorporates finely serrated teeth, whereby by alternating the directions of current flow in said windings an unbalanced magnetic field is created so the slider body may be controlled to move up or down the platen, substantially as in a conventional linear electric stepping motor. This firmness tester embodiment can accomodate essentially all sizes of fruits and vegetables without the need of special adjustments for different size ranges.

A preferred embodiment of a "hand-held" or "robotics end-effector mounted" firmness tester includes the same components as the linear motion gripper device but the vibration actuator is mounted on the outside part of said self contained frame, thereby enabling firmness measurement of very small and very large fruits in a more compact form.

This embodiment constitutes a light and handy tool for measuring the firmness of field-growing fruits such as melons or tree-growing fruits such as apples, avocado. The mid-section of the self contained frame incorporates a connector plate for attaching a long handle and trigger switch, whereby an operator can measure the firmness of fruits laying on the ground or reach fruits hanging on a tree. The same connector plate may be also employed for attaching the firmness tester as an end-effector on a robotics arm, thereby permitting automated firmness measurements in the field, grove or orchard. Portable computer means and electric rechargeable batteries for powering the firmness tester may be carried in a back pack or on a small cart towed by the operator. Motorized mobility in a plantation or grove may also be provided by mounting the batteries and the computer means on a small tractor or vehicle, while the firmness tester is attached thereto by long cable means.

The purpose of measuring firmness in the field or grove is twofold: Follow the firmness evolution of fruit or vegetable samples as they grow in order to determine the optimal harvest time for the entire crop. Selective harvesting of ripe fruits only. Thus, the firmness tester may indicate the ripeness of a fruit or vegetable in analog or digital readout form, or by an audible or visual signal in the form of two differently colored lamps or two buzzers of different frequency. A spraying nozzle is optionally provided, for automatically marking ripe fruits or vegetables by a puff of edible dye, identifying fruits or vegetables for selective manual or mechanized harvesting.

A preferred embodiment of a "linear-rotary gripper arm firmness sensor" includes the same components as the above portable firmness testers, but the vibration actuator is mounted on the periphery of a cup conveyor chainwheel, while the said first vibrating gripper body is positioned in a circular opening in the bottom portion of a cup, substantially as described in my U.S. Pat. No. 4,884,696. The advantage of this new embodiment is a provision for said second gripper body to move in a linear and rotary trajectory, or in a combination thereof. To this end, the said linear electric stepping motor platen is mounted on the side of said chainwheel, opposite the vibration actuator, while said rotary stepping motor is attached to the slider or forcer body of said linear electric stepping motor device. This enables automatic adaptation of the gripper system to any fruit size, by linear approach of said second gripper body toward said first gripper body, as a fruit is clamped between them for firmness testing, while the release of the fruit from the cup, after the test, is effected by the rotary motion of the gripper arm, driven by the rotary stepping motor.

A preferred embodiment of a simpler "manually adjustable rotary gripper arm firmness sensor" comprises a vibration actuator mounted on the periphery of a cup conveyor chainwheel, while the said first vibrating gripper body is positioned in a circular opening in the bottom portion of a cup, substantially as described in my U.S. Pat. No. 4,884,696, however in this simpler new embodiment a height adjustable rotary electric stepping motor is employed, enabling easy adaptation of the firmness sensor to different fruit or vegetable size ranges. Still another preferred embodiment of a simplified "manually operated linear motion gripper arm table-top firmness tester" employs a spring and ballast weight mechanism for positioning the gripper arm while controlling the gripping force on the tested object.

In all said embodiments, the gripper surfaces in contact with the fruit or vegetable may be in the form of convex, concave or flat surfaces. Flat and concave surfaces have the advantage of providing a larger contact area for exciting the fruit, as well as transmitting the signals to the acceleration transducers, thereby increasing the sensitivity of the firmness tester. Convex surfaces facilitate better repeatability of firmness readings taken on different sights on the same fruit, because the contact areas vary much less, even when the shape of the fruit is irregular, such as in Red Delicious apples.

SHORT DESCRIPTION OF THE DRAWINGS

DETAILED DESCRIPTION OF THE DRAWINGS

Figure 1:
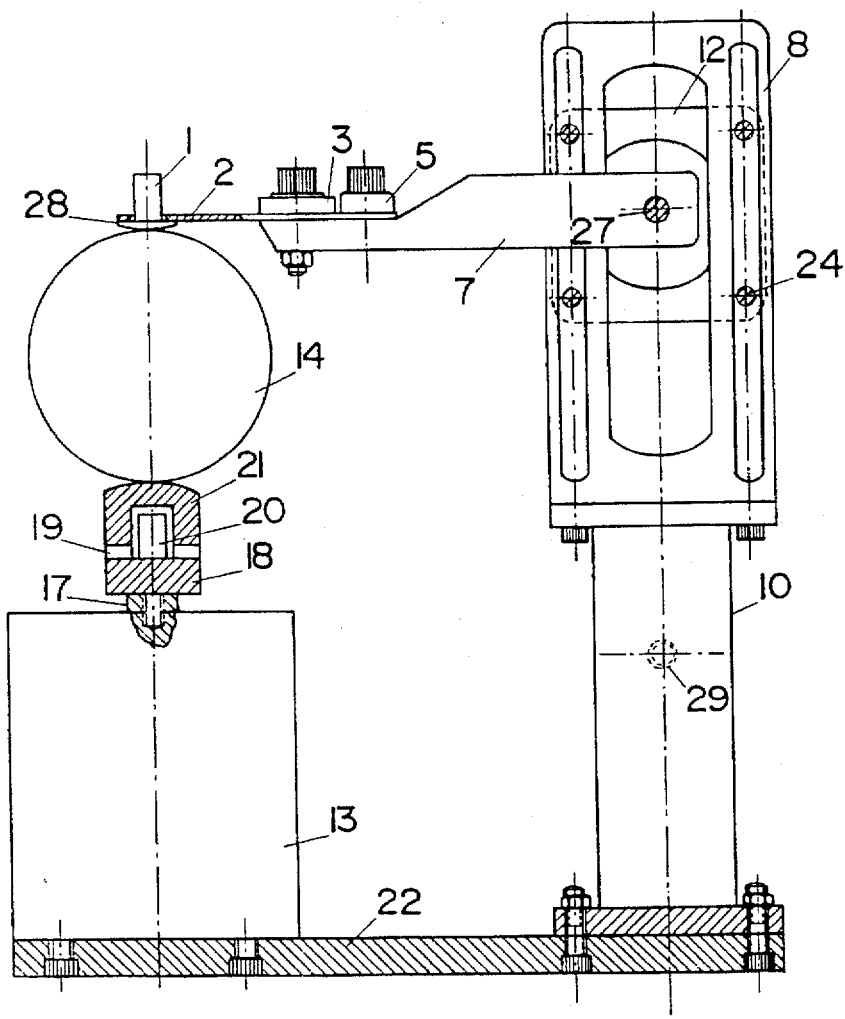
FIG. 1 is a side view and part section of an "automatic rotary gripper arm table-top firmness tester" employing rotary motion of the gripper arm, by a rotary electric stepping motor.
Figure 2:
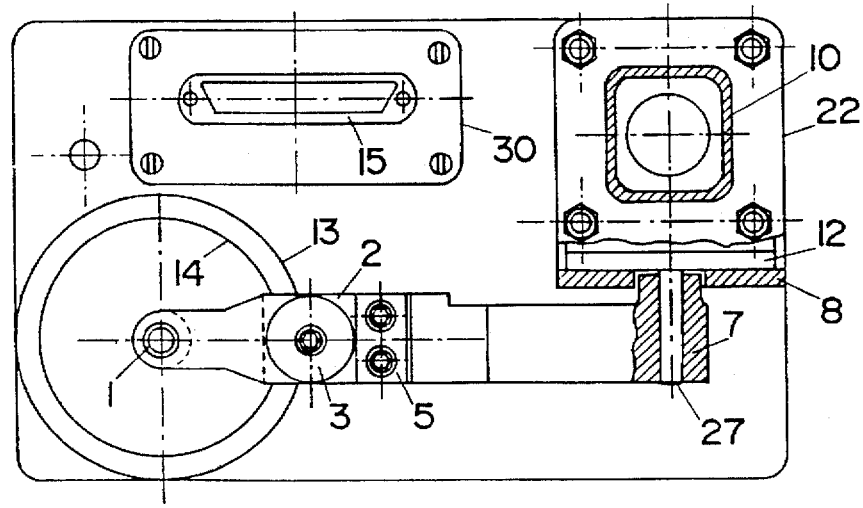
FIG. 2 is a top view and part section of the tester shown in FIG. 1.

Referring now to FIGS. 1 and 2 of the drawings, an automatic rotary gripper arm table-top firmness tester comprises a vibrator assembly and an object-holding assembly mounted on a flat base 22. The vibrator assembly comprises a vibration actuator 13 and table 18 bolted to a spigot 17. A first lower gripper body 21 mounted on top of the table 18 incorporates a convex gripper surface for contacting the bottom of the tested object 14. The gripper body encloses a first input acceleration transducer 20 mounted on the table 18, whence the wires from the transducer 20 are fed through side canals 19 in the gripper body 20. At the other end of the base 22 a vertical pedestal post 10 carries at its top the object-holding assembly which includes a rotary electric stepping motor 12, height-adjustable by means of slotted brackets 8 and screws 24. A gripper arm 7 is mounted on the motor shaft 27 and holds the root end of a leaf-spring 2 by means of a bracket and bolts 5. A second upper gripper body 28 incorporating a convex contacting surface, is attached to the underside of the free end of the leaf spring 2, which incorporates a hole enabling attachment of a second output acceleration transducer 1, directly to the topside of the upper gripper body 28, thereby minimizing the path of the vibration signal from the fruit 14 to the acceleration transducer 1. A sensor means 3, for monitoring the force or pressure exerted by the gripper body 28 on the fruit 14 is attached to the leaf spring 2. This sensor means may be in the form of a load cell incorporating strain gauges within, or the strain gauges may be attached directly on the leaf spring proper. A toggle switch 29 is mounted on the pedestal post 10 for starting and stopping the stepper motor in the clockwise and counter clockwise directions, as required for the firmness measurement operation. A hollow recess in the base 22 (not shown in the drawings) is adapted to contain the wiring and electronic circuit board incorporating signal conditioning and internal computer means. A cover 30 to said recess in the base 22 incorporates a connector 15 for attaching a multi-lead cable to a power supply or rechargeable batteries and readout devices or external computer means if any.

Figure 11:
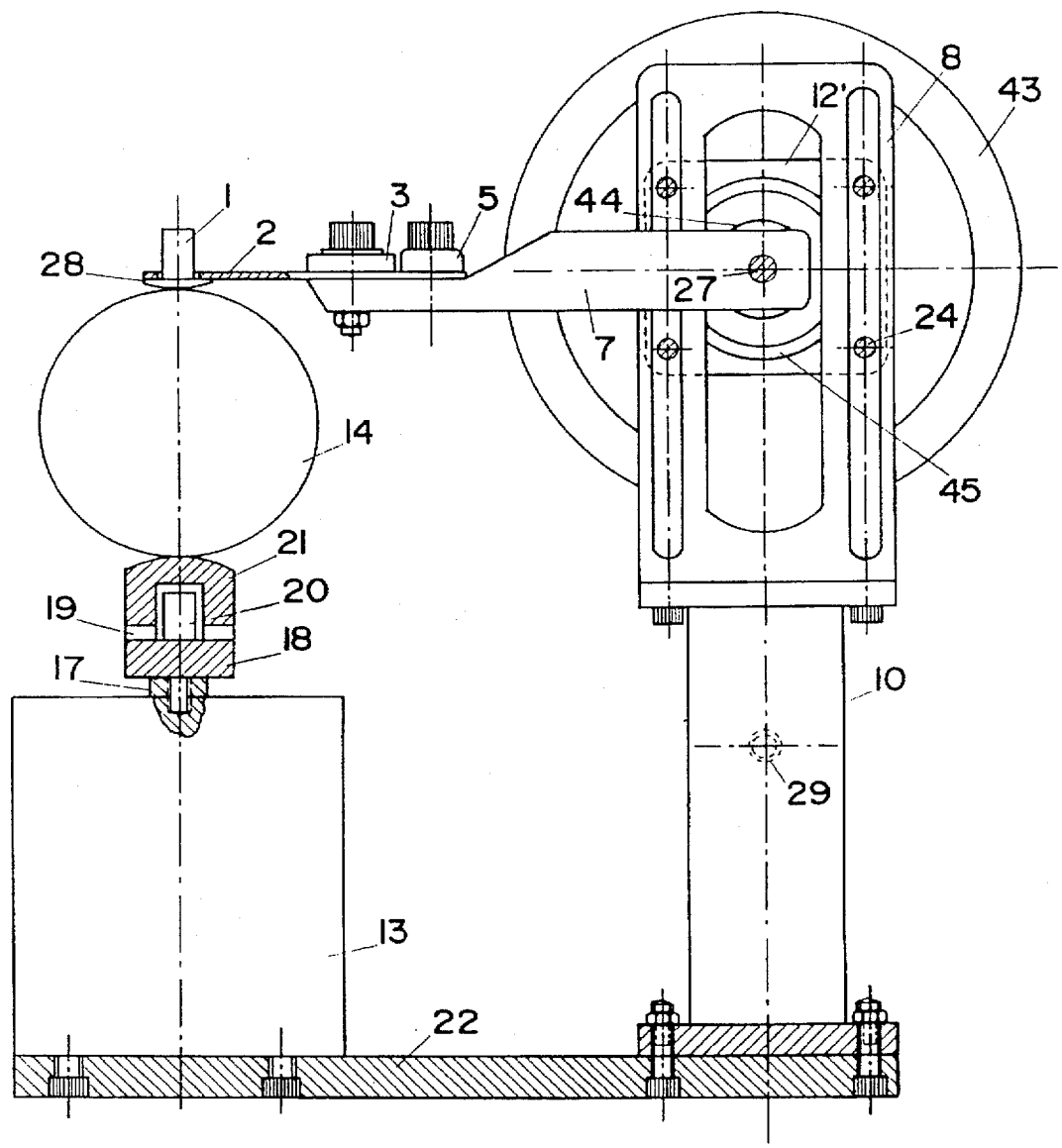
FIG. 11 is a side view and part section of a "manually operated rotary gripper table-top firmness tester" employing rotary motion of the gripper arm by a hand operated wheel.

A simpler version of the rotary gripper arm table-top firmness tester is shown in FIG. 11, wherein in lieu of said rotary electric stepping motor the gripper arm 7 is rotated manually by a wheel 43, attached to the gripper arm shaft 27. The shaft 27 is running in two ball bearings 44 mounted in a height adjustable bearing housing 12', similarly to said rotary electric stepping motor 12. For maintaining an accurate gripping force during the firmness measurement interval, a permanent magnet brake assembly 45 is attached between said bearing housing 12' and shaft 27. The purpose of the magnetic brake assembly is to hold the gripper arm 7 in position, once the preset gripping force is attained, rather than relying on a steady hand of the operator.

Figure 3:
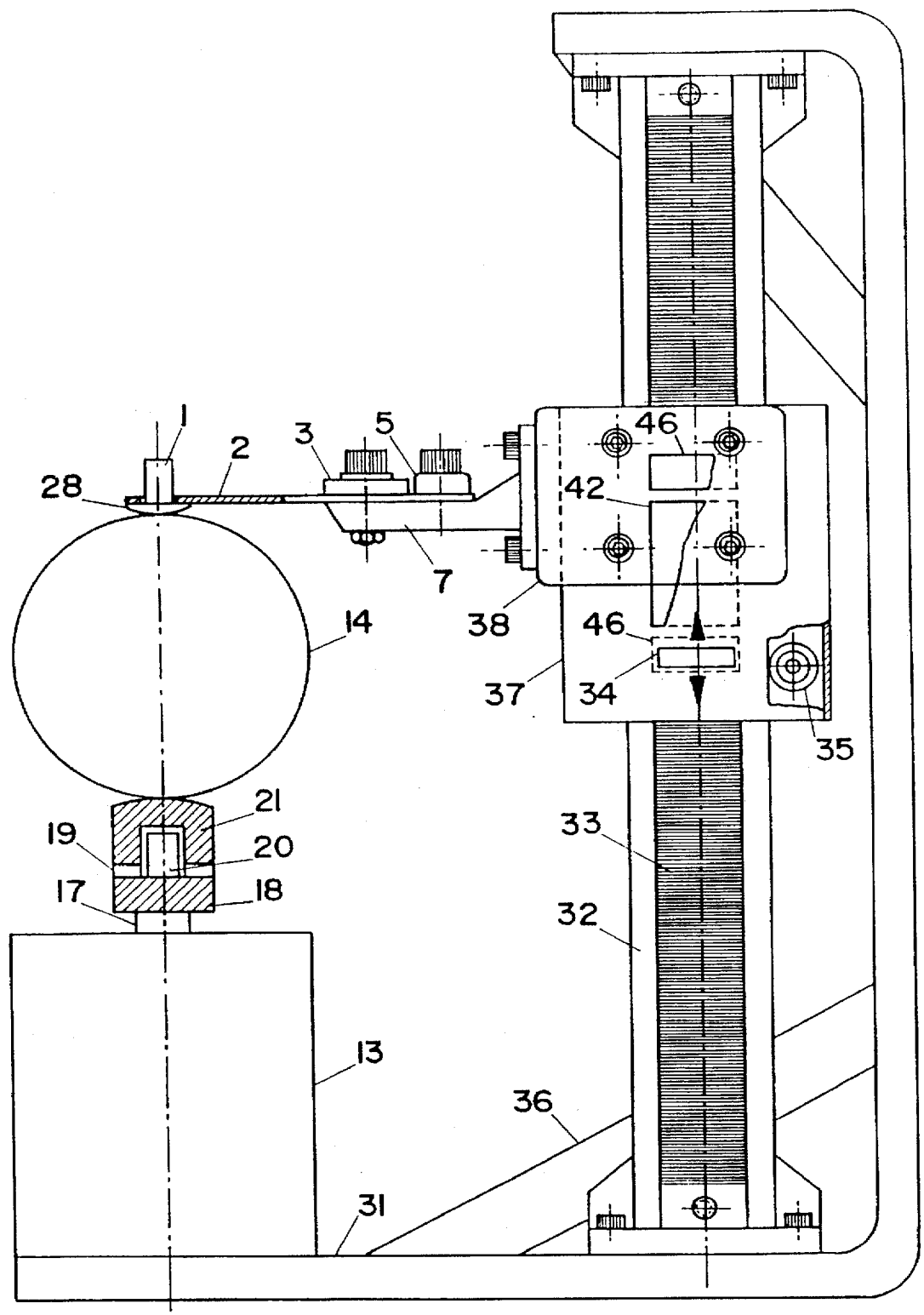
FIG. 3 is a side view and part section of a "table-top" firmness tester featuring automatic or manual linear motion of the gripper arm, by a linear electric stepping motor device or hand operated lever respectively.

A linear motion gripper arm table-top firmness tester is shown in FIG. 3, wherein the vibrator assembly is the same as in the previous firmness testers of FIG. 1 and FIG. 2. The lower horizontal part of the self contained frame 31 serves the same functions as the base 22 in FIG. 1 and 2 while its vertical part, reinforced by braces 36, incorporates a vertical platen 32 and slider body 37. The leaf spring 2 and gripper body 28, as well as the fruit contacting end of the gripper arm 7 are also the same as in FIG. 1 and 2 but its other end is attached to a bracket 38 bolted to the slider assembly 37 which is guided along the platen 32 by rows of hardened steel balls or miniature ball bearing rollers 35, traveling on the sides of the platen 32. A strong permanent magnet 42 incorporated in the slider body 37 causes it to be attracted to the platen 32 at all times, essentially serving as a magnetic brake, so that the slider position along the platen is fixed unless it is displaced from this position by an external force, which is stronger than the magnetic field forces. For gripping a fruit or vegetable 14, the slider assembly 37 may be moved up or down the platen 32 manually by the lever 34, or automatically, by incorporating a pair of windings 46, in the slider body 37, one on each side of the permanent magnet 42. This arrangement is essentially the same as in a "forcer" of a standard linear electric stepping motor, wherein an unbalanced magnetic field is created by alternating the direction of the current flow in the windings 46. Serrated teeth 33 fabricated on the surface of the platen 32 enable micro-stepping of the slider body 37 along the platen 32, as in a standard linear stepping motor. This firmness tester can accomodate essentially all sizes of fruits and vegetables without the need of special adjustments for different size ranges.

Figure 12:
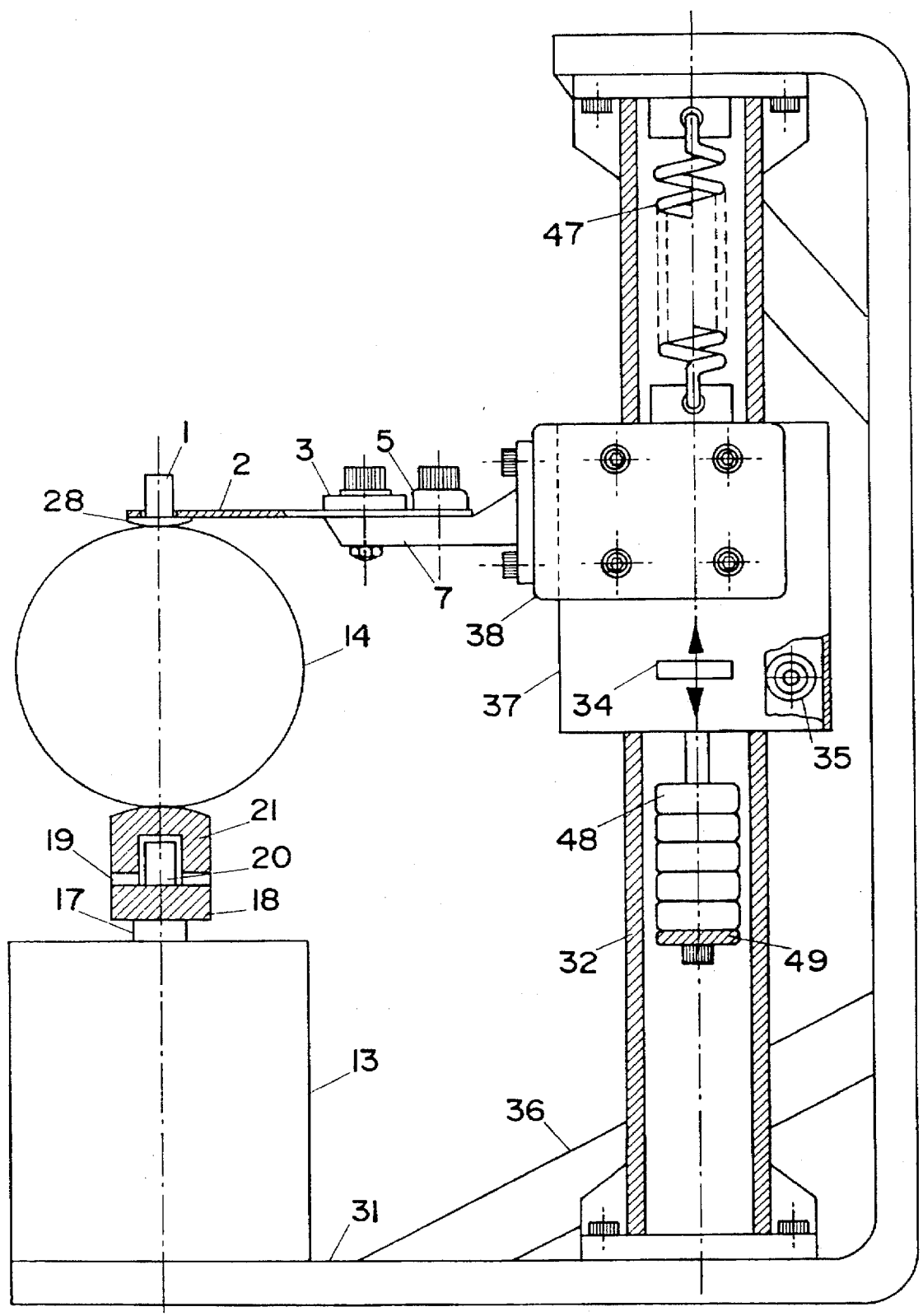
FIG. 12 is a side view and part section of a "manually operated linear motion gripper arm table-top firmness tester" wherein the position of the gripper arm and the gripping force on the tested object are controlled by a spring and ballast weight mechanism.
Figure 13:
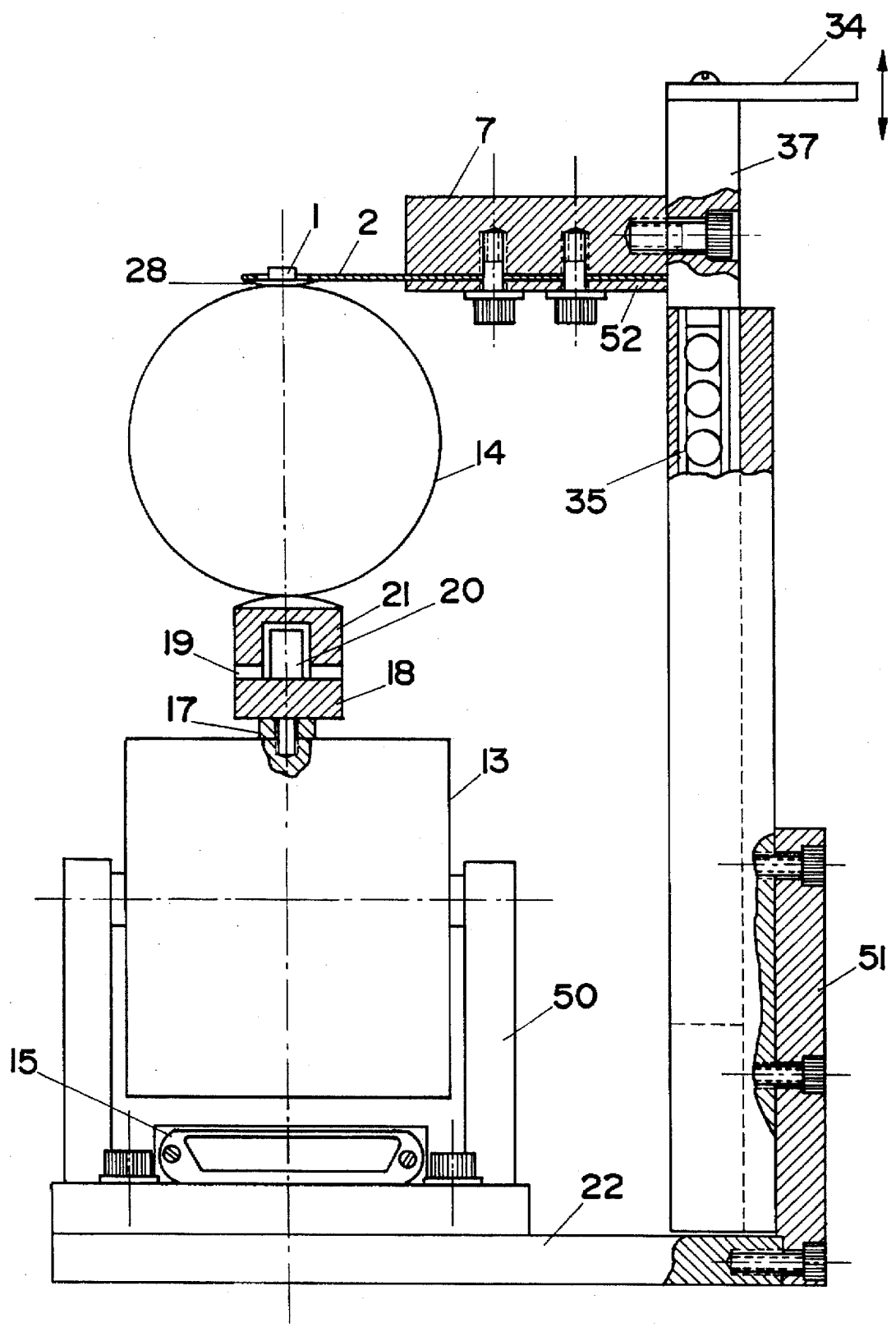
FIG. 13 is a side view and part section of a "manually operated linear motion gripper arm table-top firmness tester", wherein the gravity force of the preset combined weight of the gripper arm and the slider body is used to apply a predetermined gripping force on the tested object.

Two versions of manually operated linear motion gripper arm table-top firmness testers are shown in FIGS. 12 and 13. In the version of FIG. 12, the position of the gripper arm and the gripping force on the tested object are controlled by a spring 47 and variable mass counter-weights 48, attached to the slider body 37 by a bolt and disk plate 49. For a given fruit size range, the mass of the counter weights stretching the spring 47, may be adjusted so that the gripper surface 28 repeatedly applies a preset gripping force to the fruit 14. In the simpler version of FIG. 13 a purely gravitational force is used for gripping the fruit 14 between the gripping surfaces 21 and 28, e.g. by the combined weight of the gripper arm assembly 7, plate 52 and the relatively longer slider body 37, which may be moved up or down by the lever 34, on two sets of steel ball bearing races 35. Note that the operation of the version in FIG. 12 is identical to the operation of the version in FIG. 13, if the spring 47 is removed from the version in FIG. 12. In these simple firmness testers the gripping force must be preset for any given fruit or vegetable variety, by the weights 48 in the version of FIG. 12 or by the size of the gripper arm block 7, in the version of FIG. 13.

Operation of the table-top firmness testers depicted in FIGS. 1, 2, 3, 11, 12 and 13 is as follows:

The edible object 14 is placed onto the vibrating gripper surface 21 while the movable gripper surface 28 is brought into contact with the other side of the object 14, urging it onto the vibrating surface 21. The motion of the movable gripper surface 28 may be effected automatically or manually, by a rotary or linear trajectory, as depicted in FIG. 1, 3, 11, 12 and 13. In the automatic mode a rotary or linear electric stepping motor is employed to effect the movement of the gripper arm 7, whence the firmness testing cycle is completed automatically once the switch 29 is pressed. As the surface of the movable gripper 28 touches the fruit 14, the signal emitted by the gripper force sensing means 3 increases, as the clamping force increases with further movement of the gripper arm 7. This signal is used in a feedback control loop of the electric stepping motor, whereby it stops as soon as the gripping force reaches a preset value, signalling that the object-holding assembly is properly gripping a fruit. The magnitude of the firmness index is then computed, displayed and/or recorded by computer means, as described later. The magnitude of the preset gripping force is just sufficient to sense the transmitted vibration signal from the fruit 14 by the acceleration transducer 1, but too small to cause any damage to the tested fruit or vegetable.

In the manual mode, the gripper arm 7 is slowly moved while the output of the gripper force sensor means 3 is monitored on a first readout device. Once the preset gripping force is reached, the operator stops the movement of the gripper arm 7 and observes the firmness index value on a second readout device. Better accuracy may be achieved if a permanent magnet brake is incorporated, as described above, whereby the gripper arm is kept stationary at the preset gripper force, allowing prolonged observation and/or recording of the firmness index.

In the simpler versions of the linear motion firmness testers in FIG. 12 and FIG. 13, the slider body 37 and gripper arm 7 are simply raised by one hand using lever 34, while the fruit 14 is placed onto the lower gripper surface 21 by the other hand, then the upper gripper assembly is gently lowered onto the fruit 14 whereupon a firmness reading is initiated by pressing the toggle switch 29.

Figure 4:
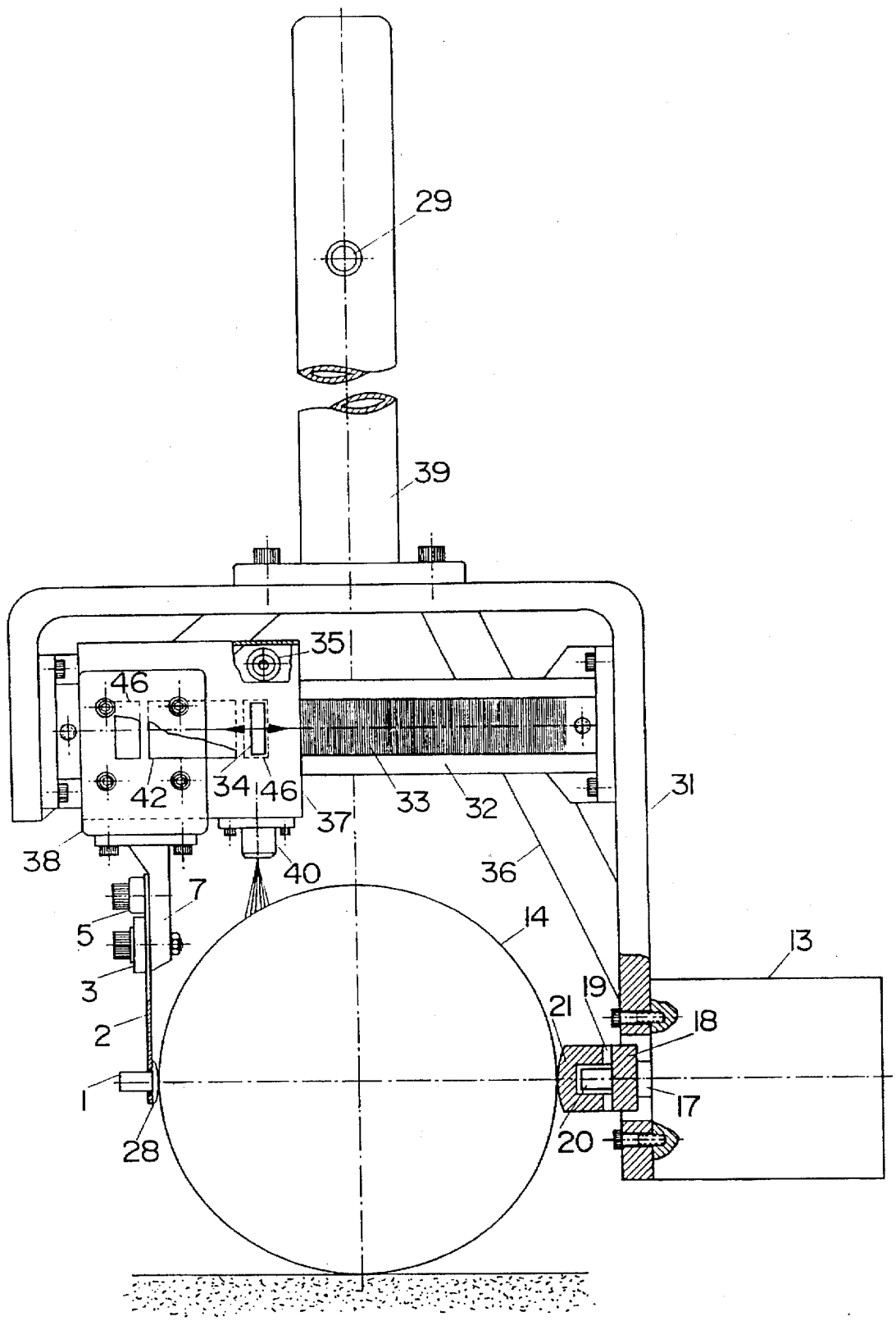
FIG. 4 is a side view and part section of a "hand-held" or "robotics end-effector mounted" firmness tester, employing linear motion of the gripper arm by a linear electric stepping motor, exemplifying firmness measurement of field-grown fruits, such as melons.
Figure 5:
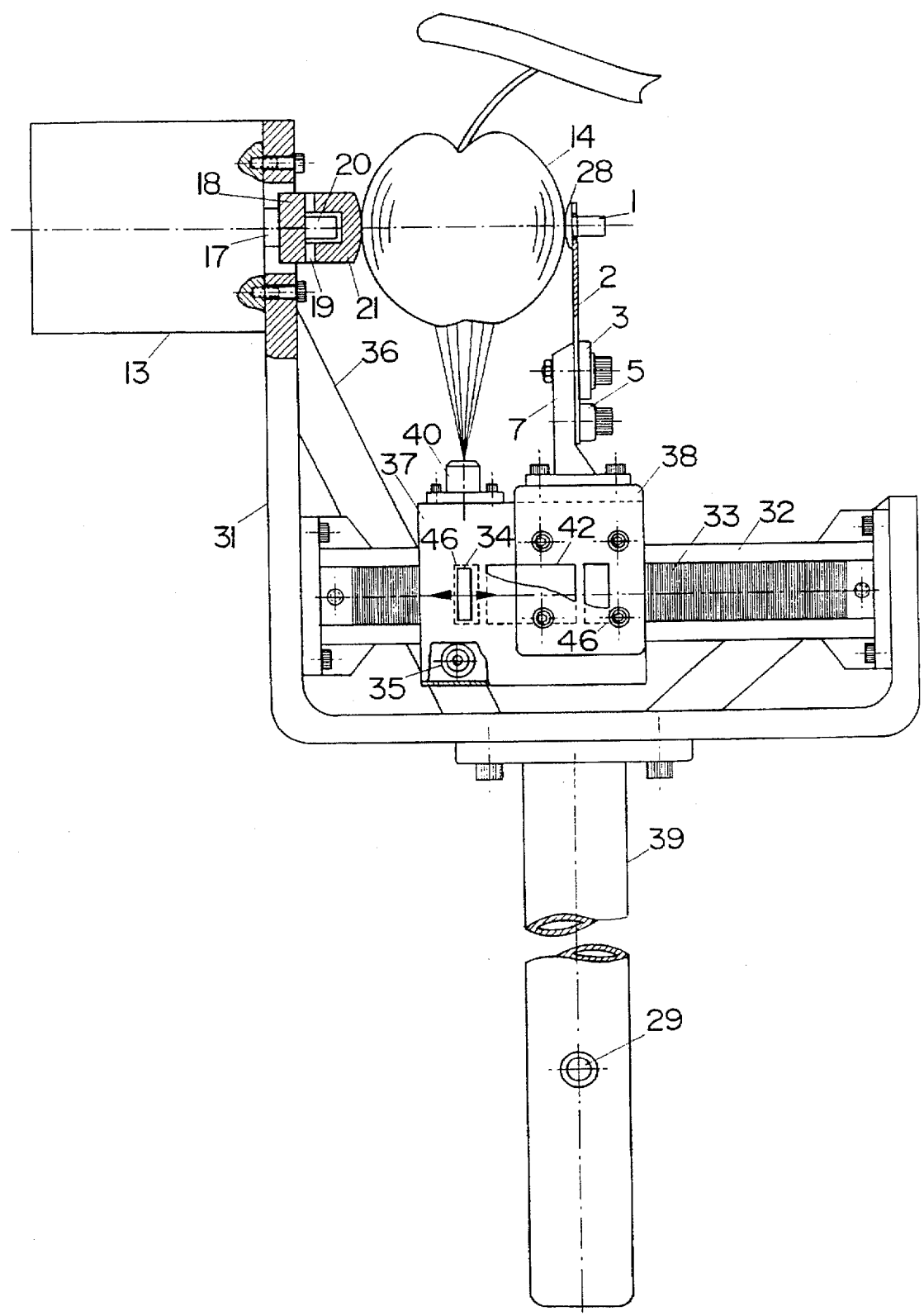
FIG. 5 is a side view and part section of a "hand-held" or "robotics end-effector mounted" firmness tester employing linear motion of the gripper arm by a linear electric stepping motor, exemplifying firmness measurement of tree-grown fruits, such as avocado or apples.

FIGS. 4 and 5 show "hand-held" or "robotics end-effector mounted" firmness testers which include the same components as the "linear gripper motion table-top firmness tester" of FIG. 3, but here the vibration actuator 13 is mounted on the outside part of the self contained frame 31, thereby enabling firmness measurement of very small and very large fruits in a more compact form. These testers are light and handy tools for measuring the firmness of field-growing fruits such as melons, as depicted in FIG. 4 or tree-growing fruits such as apples, avocado, as shown in FIG. 5. The mid-section of the self contained frame 31 incorporates a connector plate for attaching a long handle 39 incorporating the trigger switch 29, or for attaching the firmness tester by a telescopic pole, as an end-effector on a robotics arm, thereby permitting automated firmness measurement of fruits and vegetables in the field, grove or orchard. Light weight of the hand-held versions is achieved by using aluminum for manufacturing the structural components, while the computer means and electric rechargeable batteries for powering the firmness tester may be carried in a back pack or on a small cart towed by the operator. Motorized mobility in a plantation or grove may also be provided by mounting the batteries and the computer means on a small tractor or vehicle, while the firmness tester is attached thereto by long cable means.

The operation of the hand-held firmness testers in FIG. 4 and 5, is very similar to the table-top version of FIG. 3, except that here, the self contained frame 31 must be positioned so that the gripping surfaces 21 and 28 are approximately located on the equator of the fruit lying on the ground, as in FIG. 4, or hanging on a tree or vine, as in FIG. 5. These firmness testers may indicate the ripeness of a fruit or vegetable in analog or digital readout form, which may be recorded by said portable computer means, or by an audible or visual signal in the form of two differently colored lamps or two buzzers of different frequency. A spraying nozzle 40 may be incorporated, for automatically marking ripe fruits or vegetables by a puff of edible dye. These identification marks may then be used for manual or mechanized selective harvesting.

Figure 9:
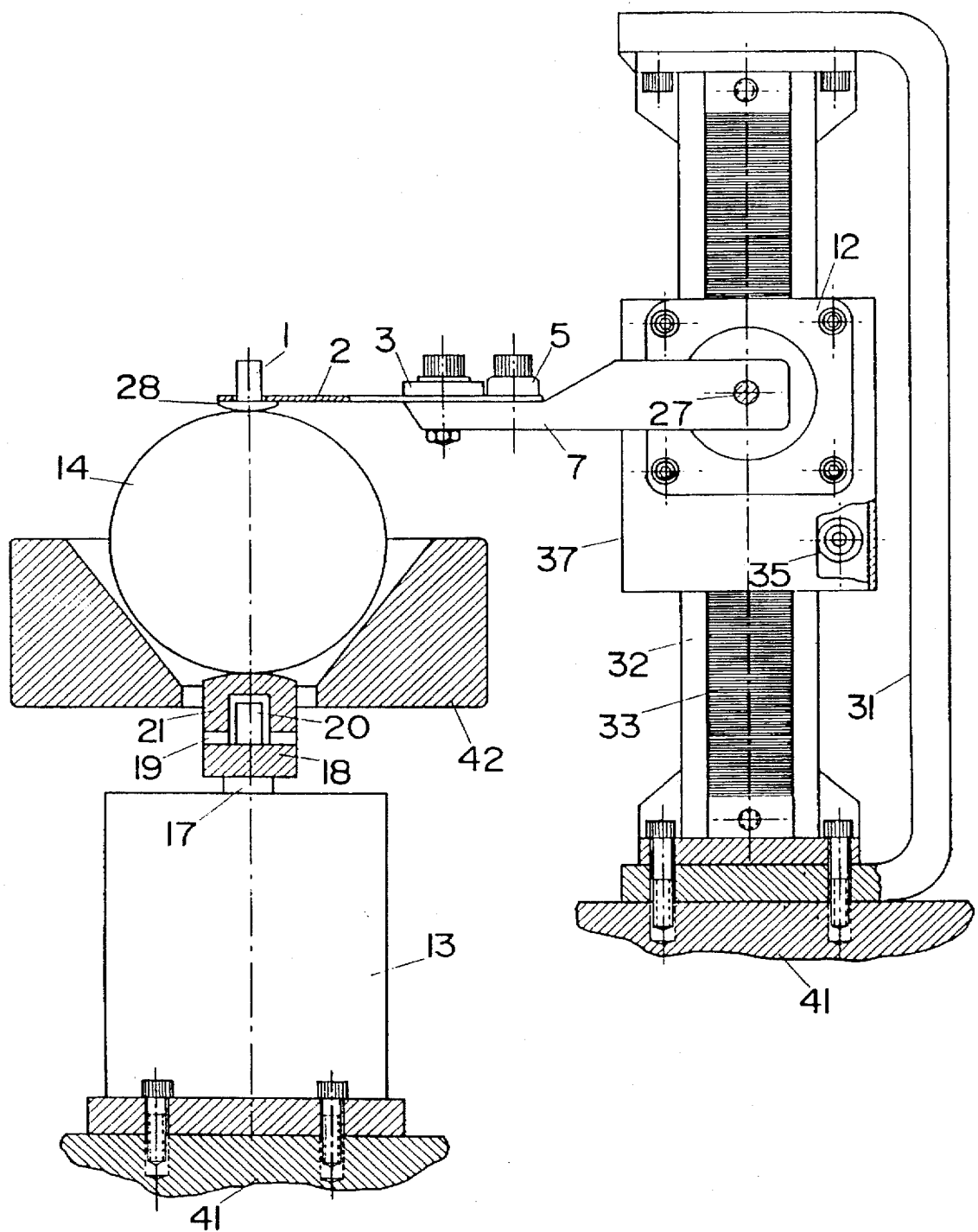
FIG. 9 is a side view and part section of a "firmness sensor" on a cup conveyor chain wheel, combining linear and rotary motion of the gripper arm, by a rotary electric stepper motor, mounted on the forcer body of a linear stepping motor.

A "rotary-linear gripper arm firmness sensor" illustrated in FIG. 9 includes the same vibrator assembly as in FIGS. 1, 2, 3, 4 and 5, while the object holding assembly is substantially a combination of the components in the firmness testers of FIGS. 1, 2 and 3. With reference to FIG. 9, here the vibration actuator 13 is mounted on the periphery of a cup conveyor chainwheel 41, while the said first vibrating gripper body 21 is positioned in a circular opening in the bottom portion of a cup 42, substantially as described in my U.S. Pat. No. 4,884,696. The advantage of this new embodiment is a provision for said gripper arm 7 and second movable gripper body 28, to move in a linear and circular trajectory, or in a combination thereof. To this end, said self contained frame incorporating said linear electric stepping motor platen 32 is mounted on the side of said chainwheel 41, opposite the vibration actuator 13, while said rotary electric stepping motor 12 incorporating the gripper arm 7 on its shaft 27 is attached to the forcer body 37 of the linear stepping motor. This enables automatic adaptation of the gripper device for any fruit size, by linear approach of said second gripper body 28 toward said first vibrating gripper body 21, as a fruit 14 is clamped between them for firmness testing, while the release of the fruit from the cup, after the test, is effected by the circular motion of the gripper arm 7, driven by the rotary stepping motor 12.

Figure 10:
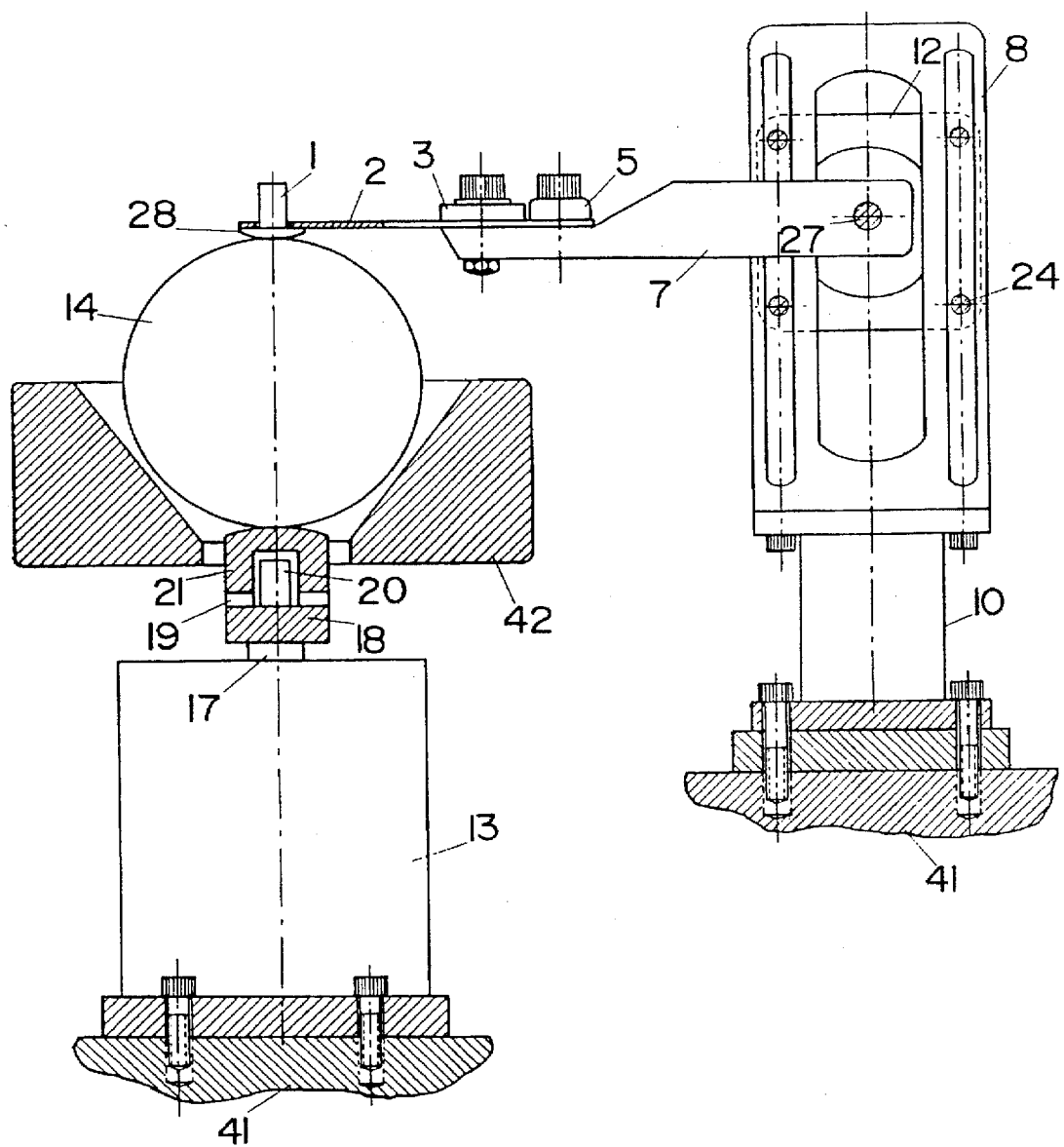
FIG. 10 is a side view and part section of a "firmness sensor" on a cup conveyor chain wheel, employing rotary motion of the gripper arm, by a height adjustable rotary electric stepping motor.

A "rotary gripper arm firmness sensor" illustrated in FIG. 10 is essentially similar in structure and operation to the firmness sensor in FIG. 9 but the object holding assembly is substantially similar to the table top firmness tester of FIGS. 1 and 2, employing rotary motion of the gripper arm 7, by a height adjustable rotary electric stepping motor 12. The vibration actuator 13 is mounted on the periphery of a cup conveyor chainwheel 41, while the said first vibrating gripper body is positioned in a circular opening in the bottom portion of a cup 42, substantially as described in my U.S. Pat. No. 4,884,696, however in this improved embodiment a position adjustable rotary electric stepping motor 12 is employed, enabling easy adaptation of the firmness sensor to different fruit or vegetable size ranges, by adjusting the position of said motor 12 along the slotted bracket 8 and retaining bolts 24.

Figure 6:
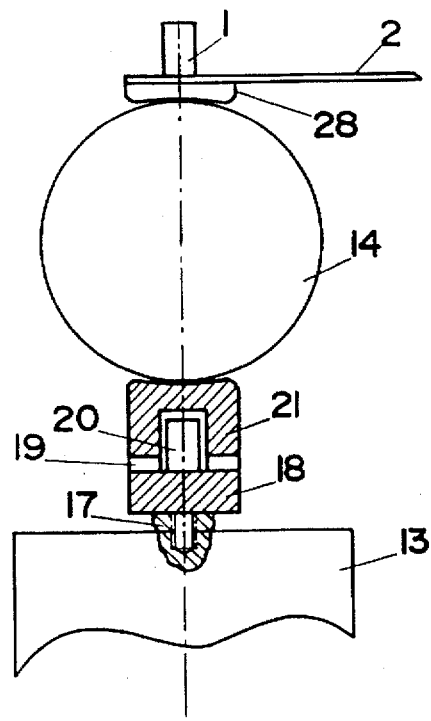
FIG. 6 shows a detail of the firmness testers and sensors in FIGS. 1 through 5 and FIGS. 9 through 12 with concave gripper surfaces.
Figure 7:
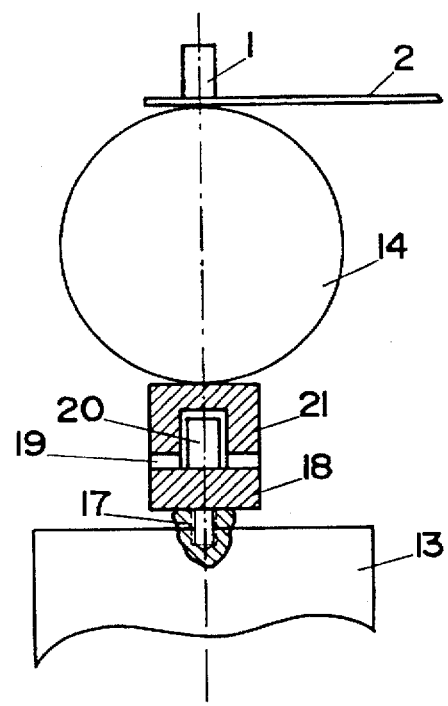
FIG. 7 shows a detail of the firmness testers in FIGS. 1 through 5 and FIGS. 9 through 12 with flat gripper surfaces.

All the "firmness testers" illustrated in FIGS. 1, 2, 3, 4, 5, 11 12 and 13 as well as the "firmness sensors" in FIG. 9 and FIG. 10, are shown with convex gripper contacting surfaces 21 and 28. The details in FIGS. 6 and 7 show alternative gripper surfaces. In FIG. 6 the contacting surfaces of the gripper bodies 21 and 28 are concave, while in FIG. 7 they are flat. Moreover, the gripper body 28 is absent in FIG. 7, whereby the leaf spring surface 2 proper serves as a contacting surface.

Figure 8:
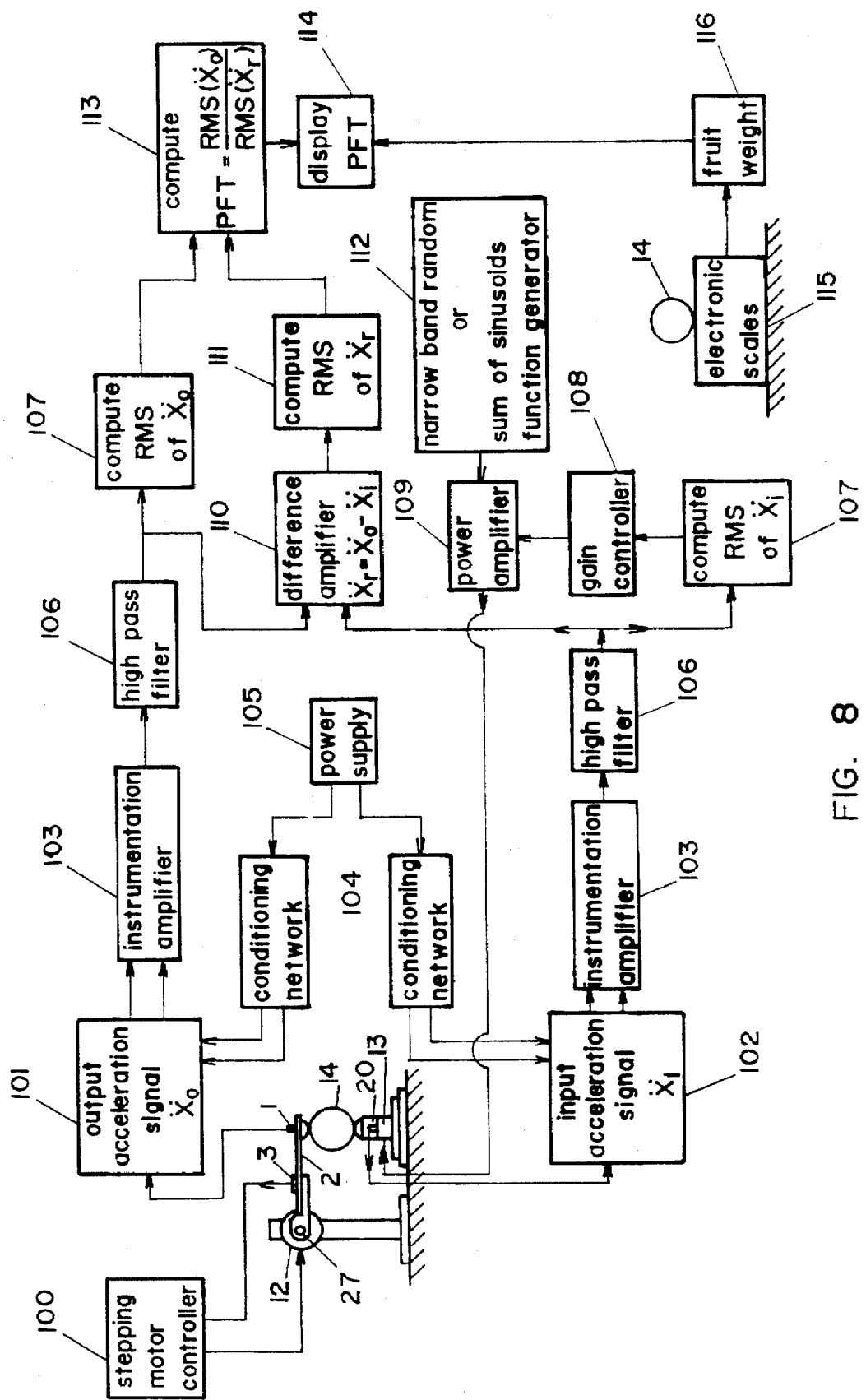
FIG. 8 is a block diagram describing the sensor conditioning, instrumentation and control electronics as well as the hardware and software of the computer means for computing a firmness index of fruits and vegetables denoted by PFT (Produce Firmness Test), as a quotient of the root mean square of the output acceleration divided by the root mean square of the relative acceleration.

FIG. 8 is a functional block diagram of the sensor conditioning, instrumentation and control electronics and computer means for computing and displaying a firmness index denoted PFT (Produce Firmness Test), by the quotient of the root mean square of the output acceleration divided by the root mean square of the relative acceleration. A common power supply 105 and separate conditioning networks 104 are provided, for the input and output acceleration transducers 20 and 1 respectively. The signal of each transducer is suitably amplified 103 and high pass filtered 106 in order to remove their dc components if any. The signals thus conditioned are fed to a difference amplifier 110 which outputs the relative acceleration signal in real time. A suitable computer means 113 then computes the root mean square values of the input, output and relative acceleration signals as well as the firmness index PFT, by said quotient of the root mean square value of the output acceleration and the relative acceleration.

This computer means may be a general purpose or dedicated digital microcomputer equipped with an analog to digital converter for acquiring the input, output and relative accelerations in digitized form.

The same computer functions may also be performed by analog circuity, incorporating standard voltage to RMS converter chips for computing the root mean square values of the input, output and relative acceleration signals. The logarithms of the RMS values of the output and relative acceleration signals may then be computed by standard log-computing chips, whereupon their quotient may be obtained as a log difference, by feeding them to a difference amplifier, the output of which may be fed into a standard anti-log chip, which will then output a signal proportional to the firmness index PFT in real time. This signal may then be displayed on a standard voltmeter readout 114, or its magnitude may be utilized to effect a decision to spray a puff of edible die through the nozzles 40 in FIGS. 4 and 5, for marking ripe fruits or vegetables. This signal may also be similarly utilized by the sophisticated computer means of the automatic firmness sorting machine described in my U.S. Pat. No. 4,884,696 for effecting classification of the inspected fruit or vegetable to the appropriate firmness grade.

The advantages of computation by analog circuity are: low cost, real time computation and extremely compact form, most suitable for the inexpensive versions of manually operated table-top and hand-held firmness testers, as well as high speed automatic machines which may employ a plurality of such sensors for sorting fruits and vegetables by firmness on a packinghouse production line. The more sophisticated automatic versions of said table-top firmness testers, require a digital stepping motor controller 100 in FIG. 8, as well as a capability to store and statistically process large datasets of firmness measurements, sometimes also in combination with weighing each fruit 14 by electronic scales 115, as schematically depicted by the lower right block in the diagram of FIG. 8. In these machines, a digital microcomputer may be combined with the analog computer means.

The signal generator function 112 which is included in the block diagram of FIG. 8, may also be implemented by a digital computer or by analog circuitry, using standard or custom made chips. The former is more bulky and expensive but versatile, whence the same firmness tester may be employed for various fruits and vegetables. The latter is compact and inexpensive but may be limited to certain fruits or vegetables, as may be required for selective harvesting of a particular cultivar by hand-held or robotics end-effector implemented firmness testers.

In any case, the function generator 112 may generate narrow band random signals or composite signals comprising sums of sinusoids with different frequency content, amplitude values and phase shifts, specifically optimized for various types of fruits and vegetables. This signal is fed to a power amplifier 109, the output of which is driving the vibration actuator 13. The gain of the power amplifier may be automatically controlled by employing the root mean square of the input acceleration as a feedback signal. Thus, the input acceleration to the tested fruit or vegetable is kept at a preset constant level, regardless of its size, mass or the spatial position of the firmness tester.

It will be understood that the firmness testers illustrated and described in the foregoing represent only examples of the many devices to be designed and built by a person skilled in the art without, however, deviating from the spirit of the invention and the scope of the appended claims. The gripper arm driving means may be alternatively implemented by pneumatic or hydraulic actuators in lieu of electric motors. The mechanical components of the equipment may be exchanged for similar, equivalent components, as long as, the principle of vibrating one point of the object and holding the diametrically opposed point is maintained, while transducer means are provided adapted to measure the input and output accelerations and to transmit respective signals to computer means.

There are also many ways to implement the functions of the block diagram of FIG. 8, by different hardware and software combinations. However, as long as, the principle of computing a firmness index as a quotient of the root mean squares of the output and relative accelerations is maintained, while using a vibration excitation signal adapted for measuring the firmness of the tested object, the foregoing descriptions represent only examples of many possible implementations, to be designed and built by a person skilled in the art without deviating from the spirit of the invention and the scope of the appended claims.

I claim:

1. A method of measuring and testing the firmness of a fruit or a vegetable in order to determine its ripeness stage comprises the steps of:

gripping said fruit or vegetable in two substantially opposite points between two bodies at a force or pressure not liable to cause damage to said fruit or vegetable;

applying a vibrational excitation onto said fruit or vegetable at one of said two opposite points by means of a vibration actuator using a narrow band random signal or a composite signal with predetermined frequency content, composed of a sum of sinusoids with frequencies, amplitudes and phase shifts specialized for the kind of fruit or vegetable to be tested;

measuring the input acceleration signal by means of a first acceleration transducer attached to said vibration actuator;

measuring the output acceleration signal by means of a second acceleration transducer at the opposite point of said fruit or vegetable;

passing the input and output acceleration signals through a difference amplifier to effect deduction of said output signal from said input signal to obtain a relative acceleration signal in real time;

feeding the obtained relative acceleration signal as well as the output acceleration signal to analog or digital computer means programmed to compute, store, indicate or display a firmness index value by dividing the root mean square of the output acceleration signal by the root means square of the relative acceleration signal.

2. Equipment for measuring and testing the firmness of a fruit or a vegetable in order to determine its ripeness stage in the form of a firmness tester or firmness sensor, comprising a vibrator assembly, a fruit-holding assembly, frame assembly, processing means, signal generation means, control means, electric power means and weighing means;

wherein said vibrator assembly includes a vibration actuator provided with a first vibrating gripper body adapted to hold and vibrationally excite said fruit or vegetable at a first point, said gripper body containing a first acceleration transducer adapted to emit an input acceleration signal in response to the vibrational excitation of the fruit or vegetable at said first point;

wherein said fruit-holding assembly includes a movable gripper body adapted to hold said fruit or vegetable at a second point approximately diametrically opposed to said first point and containing a second acceleration transducer adapted to emit an output acceleration signal in response to the vibration of the fruit or vegetable at said second point;

electrically or manually operated, mechanical means for urging said movable gripper body onto said fruit or vegetable;

spring means positioned between said movable gripper body and said electrically or manually operated urging means permitting said fruit or vegetable to be vibrated;

pressure sensing means adapted to automatically control and display the pressure or force applied to said fruit or vegetable by said electrically or manually operated urging means;

wherein said frame assembly is in the form of a flat base or self contained frame incorporating said vibrator assembly and said fruit holding assembly;

wherein said processing means includes conditioning circuitry for operating said acceleration transducers and pressure sensor means:

a difference amplifier to effect deduction of said output acceleration signal from said input acceleration signal to obtain a relative acceleration signaling in real time;

analog or digital computer means for processing the signals obtained by said acceleration transducers for obtaining said firmness index value by dividing the root mean square of the output acceleration signal by the root means square of the relative acceleration signal;

wherein said signal generation and control means includes an analog function generator or digital computer means adapted for generating narrow band random signals or composite waveform signals with predetermined frequency content, composed of a sum of sinusoids with frequencies, amplitudes and phase shifts specialized for the kind of fruit or vegetable to be tested and a power amplifier adapted to amplify said signals for driving said vibration actuator while using said input acceleration signal in a feedback loop for controlling and maintaining a preset vibration level applied to said fruit or vegetable by said vibration actuator;

wherein said electric power means includes a power supply and regulating means for operating said firmness tester or sensor and said vibration actuator, processing means, signal generation and control means and computer means;

wherein said weighing means includes electronic scales adapted to transmit a voltage signal to said computer means proportional to the weight of said tested fruit or vegetable.

3. The firmness tester or sensor as defined in claim 2, wherein said electrically operated mechanical urging means is in the form of a rotating mechanism comprising a position adjustable rotary stepping motor and solid arm with a leaf-spring clamped at one end while its other end is connected to the shaft of said rotary stepping motor;

wherein the free end of said leaf spring carries said movable gripper body and said second acceleration transducer attached thereto.

4. The firmness tester or sensor as defined in claim 2, wherein said mechanical urging means is in the form of a rotary mechanism comprising a hand-turned wheel connected to a shaft rotating in a bearing mounted in a position-adjustable housing;

wherein a magnetic brake attached to said shaft and housing maintains any preset position of said shaft and solid arm attached thereto at one end, while a leaf spring is clamped to its other end;

wherein the free end of said leaf spring carries said movable gripper body and said second acceleration transducer attached thereto.

5. The firmness tester or sensor as defined in claim 2, wherein said electrically operated mechanical urging means is in the form of a linear translation mechanism comprising a forcer and platen of a linear electric stepping motor and solid arm with a leaf-spring clamped at one end while its other end is connected to said forcer body traveling along said platen;

wherein the free end of said leaf spring carries said movable gripper body and said second acceleration transducer attached thereto.

6. The firmness tester or sensor as defined in claim 2, wherein said mechanical urging means is in the form of a linear translation mechanism comprising a hand-moved slider body traveling on rows of hardened steel balls or miniature ball bearing rollers along a platen;

wherein said slider body incorporates a magnet for the purpose of attracting the slider body to said platen so that any preset position of said slider along said platen is automatically maintained;

wherein one end of said solid arm is attached to said slider body, while a leaf spring is clamped to its other end;

wherein the free end of said leaf spring carries said movable gripper body and said second acceleration transducer attached thereto.

7. The firmness tester or sensor as defined in claims 2, wherein said electrically operated mechanical urging means is a combination of a rotary and linear translation mechanism in the form of a rotary stepping motor mounted on the forcer body of a linear stepping motor;

wherein one end of said solid arm is connected to the shaft of said rotary stepping motor while its other end carries the clamped end of a leaf spring;

wherein the free end of said leaf spring carries said movable gripper body and said second acceleration transducer attached thereto;

wherein the movement of the forcer body traveling along the platen of said linear stepping motor provides linear motion of said urging means while rotary motion is provided by the rotation of said shaft of the rotary stepping motor.

8. The firmness tester or sensor as defined in claim 2, wherein said mechanical urging means is in the form of a linear translation mechanism comprising a hand-moved slider body traveling on rows of hardened steel balls or miniature ball bearing rollers along a platen;

wherein said slider body includes a spring at one end and ballast weights on its other end;

wherein one end of said solid arm is attached to said slider body, while a leaf spring is clamped to its other end;

wherein the free end of said leaf spring carries said movable gripper body and said second acceleration transducer attached thereto.

9. The firmness tester or sensor as defined in claim 2 in a table-top configuration;

wherein said vibrator assembly and said fruit or vegetable holding assembly are mounted on said flat base, while urging of said movable gripper body is effected by a manually or electrically operated rotary mechanism.

10. The firmness tester or sensor as defined in claim 2, in a table-top configuration;

wherein said vibrator assembly and said fruit or vegetable holding assembly are incorporated in said self contained frame;

wherein urging of said movable gripper body is effected by a manually or electrically operated linear translation mechanism in the form of a slider body or linear electric motor forcer body, traveling along a platen incorporated in said self contained frame.

11. The firmness tester or sensor as defined in claim 2, in a light hand-held configuration, or in the form of a robotics end-effector firmness sensor system;

wherein said vibrator assembly and said fruit or vegetable holding assembly are incorporated in said self contained frame;

wherein urging of said movable gripper body is effected by a manually or electrically operated linear translation mechanism;

wherein said self contained frame is mounted on a long handle or telescopic boom, adapted for reaching field-growing or tree-growing cultivars.

12. The firmness tester or sensor as defined in claim 2, in a form adapted for incorporation into an automatic machine in a packinghouse processing line;

wherein a plurality of said vibrator assemblies and said fruit or vegetable holding assemblies are mounted on the periphery of a cup-conveyor chainwheel;

wherein said vibrating gripper bodies attached to said vibrators are adapted to contact and vibrationally excite fruits or vegetables traveling in cups of said conveyor through openings in the bottom parts of said cups;

wherein urging of said movable gripper body is effected by a rotary mechanism driven by a rotary electric stepping motor.

13. The firmness tester or sensor as defined in claim 2, in a form adapted for incorporation into an automatic machine in a packinghouse processing line;

wherein a plurality of said vibrator assemblies and said fruit or vegetable holding assemblies are mounted on the periphery of a cup-conveyor chainwheel;

wherein said vibrating gripper bodies attached to said vibrators are adapted to contact and vibrationally excite fruits or vegetables traveling in cups of said conveyor through openings in the bottom parts of said cups;

wherein urging of said movable gripper body is effected by a combination of rotary and linear translation mechanism, driven by rotary and linear electric stepping motors respectively.

14. The firmness tester or sensor as defined in claim 2, wherein said pressure sensing means comprises strain gauges attached to said spring means, adapted to control the gripping position of said mechanical urging means so that the force or pressure on said tested fruit or vegetable is within a preset range.

15. The firmness tester or sensor as defined in claim 2, wherein said pressure sensing means comprises a load cell attached to said spring means, adapted to control the gripping position of said mechanical urging means so that the force or pressure on said tested fruit or vegetable is within a preset range.

16. The firmness tester or sensor as defined in claim 2, wherein electric power is obtained from a AC power supply.

17. The firmness tester or sensor as defined in claim 2, wherein electric power is obtained from rechargeable batteries.

18. The firmness tester or sensor as defined in claim 2, wherein the contacting surface of said vibrating gripper body is flat, concave or convex, adapted to the typical shape and size of the kind of fruit or vegetable to be tested.

19. The firmness tester or sensor as defined in claim 2, wherein the contacting surface of said movable gripper body is flat, concave or convex, adapted to the typical shape and size of the kind of fruit or vegetable to be tested.

20. The firmness tester or sensor as defined in claim 2, wherein said computer means is an external general purpose microcomputer or dedicated computer contained in a custom made box, connected to said firmness tester or sensor by a multi-lead cable.

21. The firmness tester or sensor as defined in claim 2, wherein said processing means is in a dedicated miniaturized form, incorporated in said frame assembly, in close proximity to said vibrator assembly and to said fruit or vegetable holding assembly.

22. The firmness tester or sensor as defined in claim 2, wherein said vibration actuator is driven by analog or digital narrow band random function generating means and a power amplifier with variable gain controlled by a potentiometer or an external voltage.

23. The firmness tester or sensor as defined in claim 2, wherein said vibration actuator is driven by analog or digital composite waveform generating means and a power amplifier with variable gain controlled by a potentiometer or an external voltage;

wherein said composite waveform with predetermined frequency content, is composed of sums of sinusoids with frequencies, amplitudes and phase shifts, specialized for the kind of fruit or vegetable to be tested.

24. The method of testing or measuring the firmness of a fruit or vegetable as described in claim 1, by the firmness tester or sensor as described in claim 2;

wherein said firmness index is compensated according to the weight of the inspected fruit or vegetable by said computer means, utilizing said voltage signal transmitted by said electronic scales, proportional to the weight of said tested fruit or vegetable.

\* \* \* \* \*